United States Patent [19]

Sam

[11] 3,987,171

[45] Oct. 19, 1976

[54] QUINOXALINE FUNGICIDES

[75] Inventor: Donnie Joe Sam, Newark, Del.

[73] Assignee: E. I. Du Pont de Nemours and Company, Wilmington, Del.

[22] Filed: Apr. 7, 1975

[21] Appl. No.: 565,853

Related U.S. Application Data

[60] Division of Ser. No. 443,198, Feb. 19, 1974, Pat. No. 3,895,011, which is a continuation-in-part of Ser. No. 366,877, June 4, 1973, abandoned.

[52] U.S. Cl. .............................................. 424/250
[51] Int. Cl.² .......................................... A01N 9/22
[58] Field of Search ................ 424/250; 260/250 Q

[56] References Cited
UNITED STATES PATENTS

| | | | |
|---|---|---|---|
| 2,479,433 | 8/1949 | Weijlard et al. | 260/250 Q |
| 3,192,212 | 6/1965 | Santilli et al. | 260/250 Q |
| 3,728,345 | 4/1974 | Cronin | 260/250 Q |

Primary Examiner—Leonard Schenkman

[57] ABSTRACT

Compounds of the formula

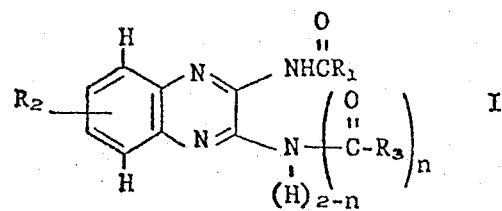

wherein $R_1$ is alkyl, alkenyl, alkynyl, cycloalkyl, alkoxyalkyl, chloroalkyl, bromoalkyl, or cyanoalkyl; $R_2$ is hydrogen, chlorine, bromine, or fluorine; $R_3$ is alkyl or alkenyl; and n is 0 or 1 are useful as fungicides. A representative compound is 3-amino-6-chloro-2-propionamidoquinoxaline.

10 Claims, No Drawings

QUINOXALINE FUNGICIDES

CROSS REFERENCE TO RELATED APPLICATION

This is a division of application Ser. No. 443,198, filed Feb. 19, 1974, now U.S. Pat. No. 3,895,011 which is a continuation-in-part of application Ser. No. 366,877, filed June 4, 1973, now abandoned.

BACKGROUND OF THE INVENTION

This invention relates to a novel class of quinoxalines and their use as fungicides. Schipper and Day describe imidazoquinoxalines in *J. Am. Chem. Soc.* 73, 5672 (1951), but no fungicidal activity of these compounds is mentioned and no quinoxalines of this invention are mentioned.

SUMMARY OF THE INVENTION

Injury to plants due to fungi is prevented by application to the locus to be protected a fungicidally effective amount of the novel compounds described below. The compounds described below have systemic fungicidal activity. Thus, the compounds can be applied directly to the plant parts to be protected, other parts of the plant, or to the media in which the plants are growing. All of these sites of application are included in the term "applying to plants" as used herein. Compositions containing these compounds are useful for controlling fungi in plants. The fungicidal compounds are quinoxalines represented by the formula:

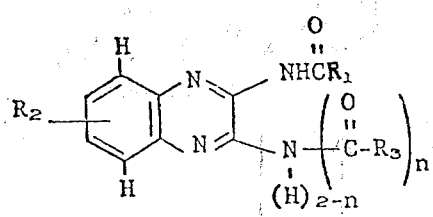

where:
$R_1$ is alkyl of 1 to 4 carbon atoms, cycloalkyl of 3 to 6 carbon atoms, alkenyl of 2 to 4 carbon atoms, ethynyl, alkoxyalkyl of 2 to 3 carbon atoms, chloroalkyl of 1 to 2 carbon atoms, bromoalkyl of 1 to 2 carbon atoms, or cyanoalkyl of 2 to 3 carbon atoms;

$R_2$ is hydrogen, chlorine, bromine, or fluorine;

$R_3$ is alkyl of 1 to 7 carbon atoms or alkenyl of 2 to 4 carbon atoms; and $n$ is 0 or 1; provided that the total number of carbon atoms in $R_1$ and $R_3$ is less than or equal to 9.

Of the $R_1$ substituents, preferred are alkyl of 1 to 2 carbon atoms when $n$ is 1; when $n$ is 0, alkyl of 2 to 3 is preferred.

Of the $R_2$ substituents, preferred is chlorine.

Of the $R_3$ substituents, preferred are alkyl of 1 to 5 carbon atoms.

Preferred are compounds where $n$ is 0.

Most preferred compounds are 3-amino-6-chloro-2-propionamidoquinoxaline and 6-chloro-3-hexanamido-2-propionamidoquinoxaline.

DESCRIPTION OF THE PREFERRED EMBODIMENTS

For the sake of clarity, the nomenclature used throughout this case is based on the position numbering system for quinoxalines shown below:

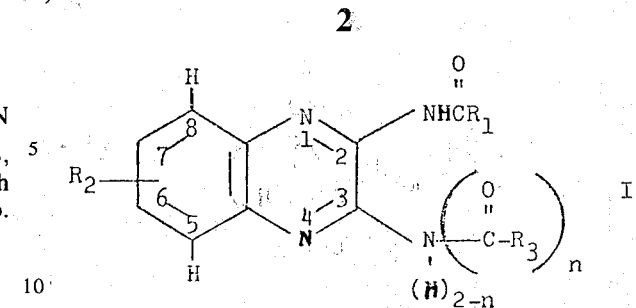

However, it should be noted that the compound may exist as such (I=Ia or II) or in other isomeric forms (compounds III, IV, V, VI, VII, and VIII) or tautomeric forms thereof, and that the isomers, tautomers, and mixtures of these isomers and tautomers are intended to be included, even though products derived from the 6- or 7-substituted diaminoquinoxalines will be named as 6-substituted compounds of type II. Obviously, compounds differing only in position of $R_2$ are the same as each other when $R_2$ is hydrogen (e.g., Ia is the same as II when $R_2$ = H).

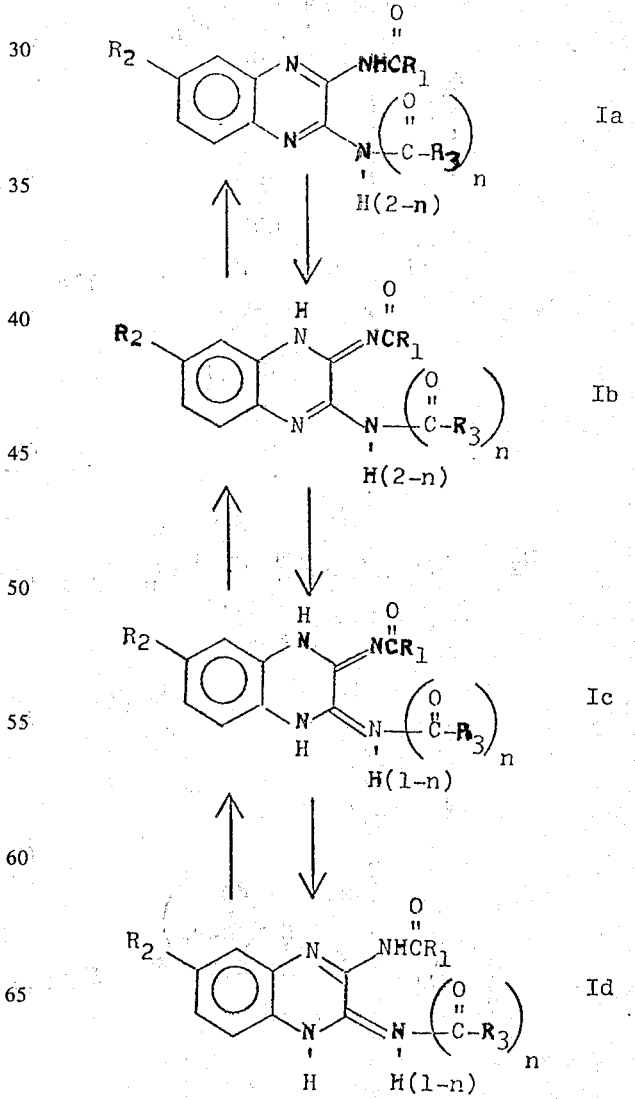

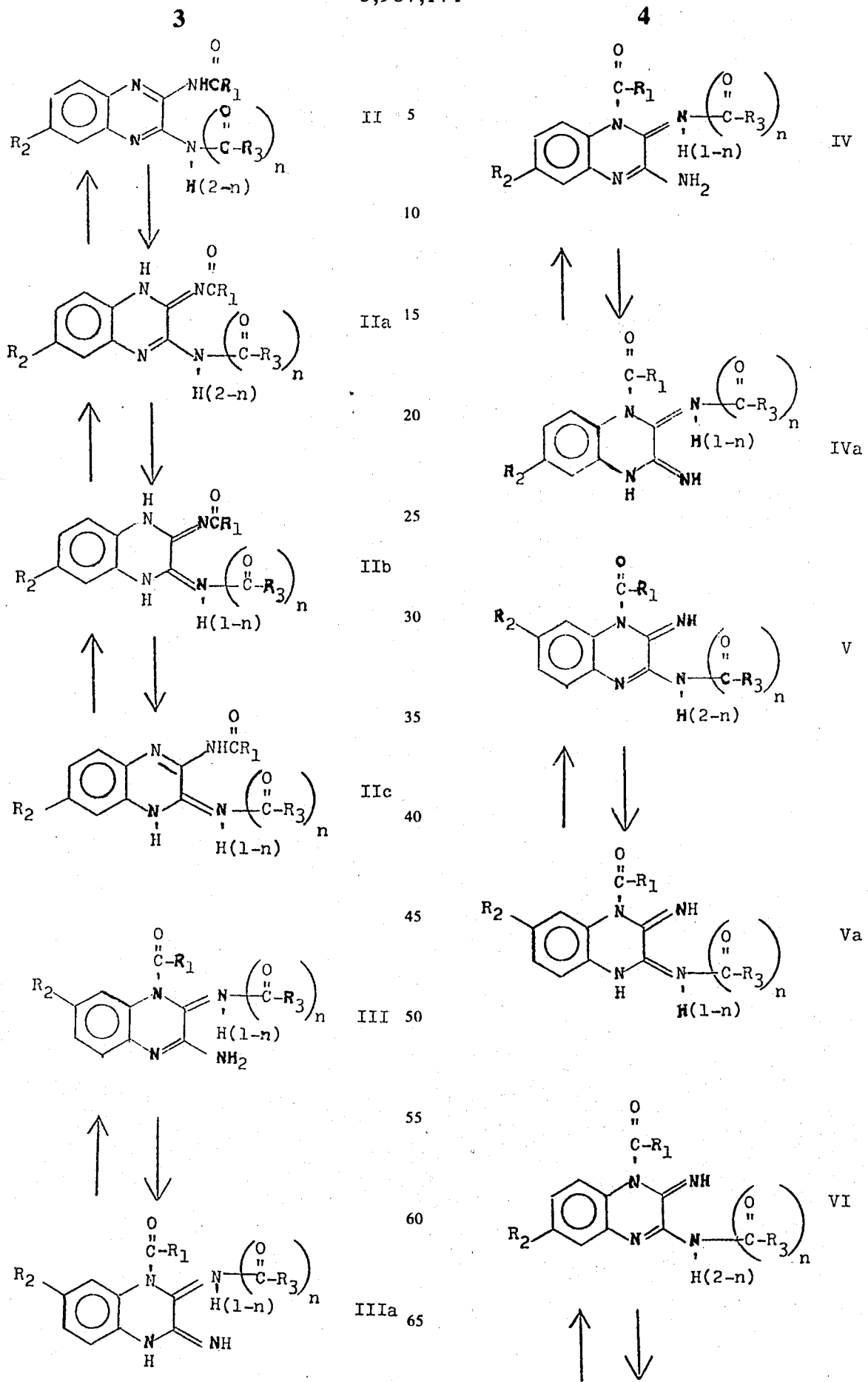

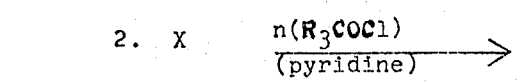

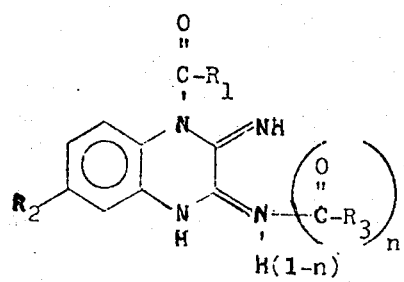 VIa

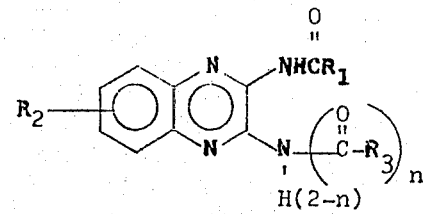

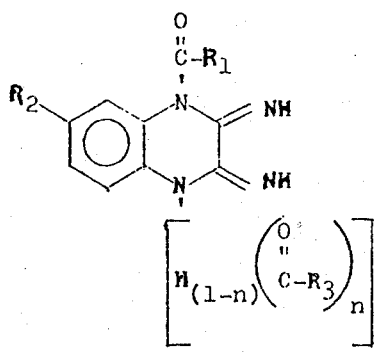 VII

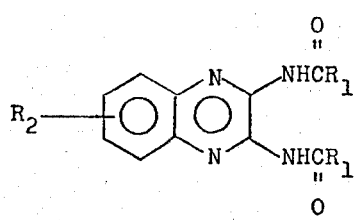

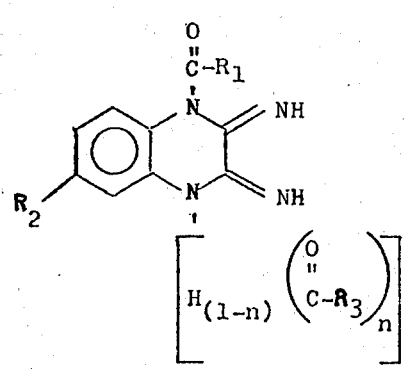 VIII

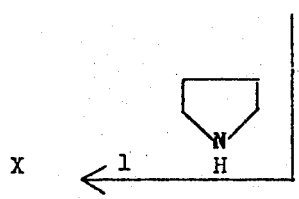

The compounds of this invention are made by the processes illustrated by the following equations, wherein the substituents are as previously defined:

1. 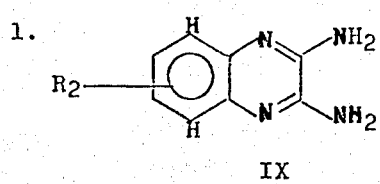

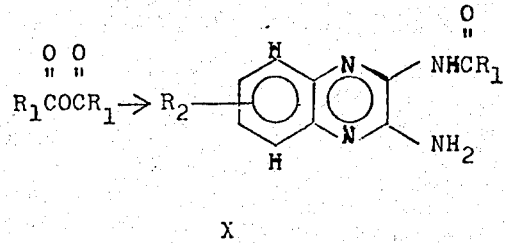

The starting material for reaction 1, a 2,3-diaminoquinoxaline (IX), is prepared as follows:

4. 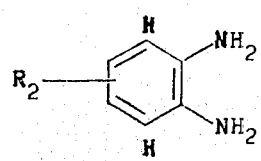

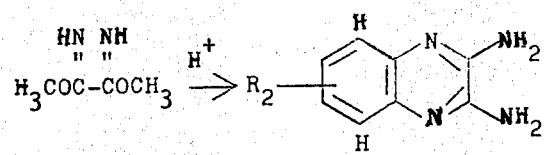

The o-phenylenediamine and substituted o-phenylenediamine reactants in the above reaction (4) are commercially available or easily synthesized by those skilled in the art. The dimethyl oxaldiimidate reactant can be prepared by the reaction of cyanogen in an excess of methanol, preferably with a basic catalyst. Temperatures and pressures in this reaction are not critical, but temperatures and pressures should be selected to handle gaseous cyanogen conveniently, as is known to those skilled in the art. Dimethyl oxaldiimidate can be isolated from the reaction mixture by distillation. The compound boils at 65° C at 43 mm pressure. The dimethyl oxaldiimidate can also be formed and reacted with the o-phenylenediamine in situ. Reaction 4 above proceeds in a methanol solvent system at room temperature. A small amount of acid is required. The preparation of 2,3-diaminoquinoxalines is also described in Hinsberg and Schwantes, Ber. 36, 4039 (1903) and Schipper and Day, J. Amer. Chem. Soc. 73, 5672 (1951).

Reaction 1 above is conveniently run at room temperature in an inert solvent, such as tetrahydrofuran, dioxane, or acetonitrile, for an overnight (ca. 15 hrs.) period. Temperature of the reaction mixture can be varied from about 15° to 35° C., reaction time from about 4 to 48 hours, and mole ratio of anhydride to diaminoquinoxaline from about 1:1 to 4:1. Order of addition of reactants is not critical. The acid anhydride can be substituted by one equivalent of the corresponding acid chloride and an acid acceptor such as pyridine. Note that Schipper and Day, J. Amer. Chem. Soc. 73, 5672 (1951) teaches that reflux of 2,3-diaminoquinoxalines with acid anhydrides produces imidazoquinoxalines. Thus, high temperatures should be avoided in reaction 1.

Reaction 2 is accomplished by permitting a compound of type X to react with an equivalent amount or slight excess of an appropriate acid chloride in the presence of an equivalent amount or excess of a tertiary amine (such as pyridine, triethylamine, or lutidine). The tertiary amine can be employed as the solvent for X during the addition of the acid chloride, or it may be added to a mixture of the acid chloride and X. The reactants can be diluted with an inert solvent such as tetrahydrofuran, dioxane, or acetonitrile; and the reaction temperature should be maintained between 0° and 25° by external cooling. A reaction time of one hour is normally sufficient.

Reaction 3 represents a convenient method for the preparation of compounds of the type XI, in which the two amide groups are identical. The reaction of two equivalents or an excess of an appropriate acid chloride with IX in the presence of two equivalents or an excess of a tertiary amine under the conditions described for reaction 2 affords compounds of the type XI. The conversion of XI to X can be achieved by the selective cleavage of one of the amide moieties. Thus, X is obtained when XI is permitted to react with one equivalent of a secondary amine such as pyrrolidine or morpholine in an inert solvent such as tetrahydrofuran or acetonitrile at ambient temperature for one to seven days.

Reaction 1 is the method of choice for the preparation of compounds of type X when $R_1$ contains from one to three carbon atoms. For the preparation of compounds of type X where $R_1$ contains more than three carbon atoms, reaction 3 is the preferred method.

In the examples which follow, all percentages and parts are by weight and temperatures in degrees centigrade, unless otherwise indicated.

EXAMPLE 1

3-Amino-6-chloro-2-propionamidoquinoxaline

A suspension of 5.0 parts of 6-chloro-2,3-diaminoquinoxaline in 75 parts of tetrahydrofuran (THF) and 15 parts of propionic anhydride was stirred overnight at room temperature. The reaction mixture was filtered and the filter cake was washed with n-butyl chloride and dried to yield 3.7 parts of yellow solid. Recrystallization from THF gave pale yellow crystals of 3-amino-6-chloro-2-propionamidoquinoxaline, m.p. 300.5°–302.5°.

EXAMPLE 2

6-Chloro-3-hexanamido-2-propionamidoquinoxaline

A suspension of 50 parts of 3-amino-6-chloro-2-propionamidoquinoxaline in 1000 parts of pyridine was cooled to 5° in an ice bath. A solution of 96 parts of hexanoyl chloride in 88 parts of tetrahydrofuran was added as quickly as possible with good cooling to prevent the temperature from rising above 25°. The reaction mixture was stirred for 10 minutes and then poured into 2500 parts of ice water. The yellow gum which separated was removed by filtration and washed with water and then dissolved in 2700 parts of methylene chloride. The methylene chloride solution was washed in succession with 1000 parts each of water, 5% aqueous hydrochloric acid, water, 10% aqueous sodium carbonate, and water. The methylene chloride solution was dried ($MgSO_4$) and evaporated. The residue was recrystallized from 1:4 ethyl acetate-benzene, the solid filtered off, and washed with ether to yield 8 parts of 6-chloro-3-hexanamido-2-propionamidoquinoxaline, m.p. 158°–160°, as a colorless solid.

EXAMPLE 3

2,3-Bis-(acetamido)-6-chloroquinoxaline

To a solution of 33 parts of acetyl chloride in 44 parts of tetrahydrofuran were added 10 parts of 6-chloro-2,3-diaminoquinoxaline. The temperature rose to 35°. The reaction mixture was cooled to 5° in an ice bath and stirred vigorously during the addition of a solution of 15 parts of pyridine in 22 parts of tetrahydrofuran. The cooling bath was removed and the reaction mixture was stirred for 6 hours. The solvent was evaporated and the residue was partitioned between 340 parts of methylene chloride and 200 parts of water. The methylene chloride layer was separated and washed in succession with 200 parts each of water, 10% aqueous sodium carbonate, water, 3% aqueous hydrochloric acid, and water. The methylene chloride solution was dried ($MgSO_4$) and evaporated. The residue was triturated with ether, filtered off, and washed with ether to yield 1.6 parts of 2,3-bis-(acetamido)-6-chloroquinoxaline as a tan solid, m.p. 178° dec.

EXAMPLE 4

6-Chloro-2,3-bis-(valeramido)quinoxaline

A suspension of 100 parts of 6-chloro-2,3-diaminoquinoxaline in 1000 parts of pyridine was cooled to 5° in an ice bath. A solution of 152 parts of valeryl chloride in 130 parts of tetrahydrofuran was added quickly with good cooling to prevent the temperature from rising above 20°. The reaction mixture was stirred at ambient temperature for 1 hour and then poured into 2500 parts of water. The solid which separated was removed by filtration and washed with water, methanol, and then ether. The crude product was recrystallized from methanol to yield 55 parts of 6-chloro-2,3-bis-(valeramido)quinoxaline, m.p. 171°–173°, as a colorless solid.

EXAMPLE 5

3-Amino-6-chloro-2-valeramidoquinoxaline

A solution of 12 parts of 6-chloro-2,3 bis(-valeramido)quinoxaline and 2.5 parts of pyrrolidine in 220 parts of tetrahydrofuran was permitted to stand at ambient temperature for seven days. The solution was then poured into 750 parts of water and the solid which separated was removed by filtration and washed with water, pressed dry, and washed with hexane. The crude product was dissolved in 108 parts of boiling ethyl acetate and the resulting solution filtered. Upon addition of 100 parts of hexane and subsequent cooling, the solution deposited 3 parts of 3-amino-6-chloro-2-valeramidoquinoxaline as a pale yellow solid, m.p. 224°–228° C.

By the general procedures of Examples 1 through 5, by use of the appropriate starting materials, the following compounds can be prepared:

2-acetamido-3-aminoquinoxaline, m.p. 319°, dec.
3-amino-6-bromo-2-propionamidoquinoxaline
3-amino-6-fluoro-2-propionamidoquinoxaline
3-amino-2-propionamidoquinoxaline
2-acetamido-3-amino-6-chloroquinoxaline, m.p. 340° C
3-amino-2-butyramido-6-chloroquinoxaline, m.p. 270°–273° C
3-amino-2-butyramidoquinoxaline
2-acrylamido-3-amino-6-chloroquinoxaline
2-acrylamido-3-aminoquinoxaline
3-amino-6-chloro-2-crotonamidoquinoxaline
3-amino-2-crotonamidoquinoxaline
3-amino-6-chloro-2-methacrylamidoquinoxaline
3-amino-6-chloro-2-seneciamidoquinoxaline
3-amino-6-chloro-2-propiolamidoquinoxaline
3-amino-6-chloro-2-cyclopropanecarboxamidoquinoxaline
3-amino-6-chloro-2-cyclohexanecarboxamidoquinoxaline
3-amino-6-chloro-2-($\alpha$-methoxyacetamido)quinoxaline
3-amino-6-chloro-2-($\alpha$-ethoxyacetamido)quinoxaline
3-amino-2-($\alpha$-methoxyacetamido)quinoxaline
3-amino-6-chloro-2-($\alpha$-chloroacetamido)quinoxaline
3-amino-2-($\beta$-bromopropionamido)-6-chloroquinoxaline
3-amino-6-chloro-2-($\alpha$-cyanoacetamido)quinoxaline
3-amino-6-chloro-2-($\beta$-cyanopropionamido)quinoxaline
3-amino-6-chloro-2-($\beta$-chloropropionamido)quinoxaline
3-amino-2-($\alpha$-bromoacetamido)quinoxaline
2,3-bis((acetamido)quinoxaline
3-amino-6-chloro-3-octanamidoquinoxaline
2,3-bis(propionamido)quinoxaline
2,3-bis(acetamido)-6-fluoroquinoxaline
6-bromo-2,3-bis(propionamido)quinoxaline
6-chloro-2,3-bis(propionamido)quinoxaline
2,3-bis(butyramido)-6-chloroquinoxaline
6-chloro-2,3-bis(isobutyramido)quinoxaline
3-acetamido-6-chloro-2-propionamidoquinoxaline
6-chloro-2-cyclopropanecarboxamido-3-propionamidoquinoxaline
6-chloro-2-cyclopentanecarboxamido-3-propionamidoquinoxaline
2,3-bis(acrylamido)-6-chloroquinoxaline
6-chloro-2,3-bis(crotonamido)quinoxaline
6-chloro-2-acetamido-3-seneciamidoquinoxaline
6-chloro-2-crotonamido-3-propionamidoquinoxaline
6-chloro-2-propiolamido-3-propionamidoquinoxaline
6-chloro-2-($\alpha$-methoxyacetamido)-3-propionamidoquinoxaline
6-chloro-2-($\alpha$-ethoxyacetamido)-3-propionamidoquinoxaline
6-chloro-2-($\alpha$-chloroacetamido)-3-propionamidoquinoxaline
6-chloro-2-($\beta$-chloropropionamido)-3-propionamidoquinoxaline
2-($\alpha$-bromoacetamido)-6-chloro-3-propionamidoquinoxaline
2-($\alpha$-bromopropionamido)-6-chloro-3-propionamidoquinoxaline
6-chloro-2-($\alpha$-cyanoacetyl)-3-propionamidoquinoxaline
6-chloro-2-($\beta$-cyanopropionamido)-3-propionamidoquinoxaline The compounds of this invention possess outstanding fungicidal activity when employed to prevent or mitigate damage to plants by fungi. The compounds are particularly effective against powdery mildew fungi, Erysiphaceae. Plants are protected by preventive (before infection) and curative (after infection) treatments. Disease control is provided throughout a plant by systemic action. Isolated treatments protect across (from ventral to dorsal and dorsal to ventral) a leaf and both acropetal (upward) and basipetal (downward).

The compounds of this invention control a wide variety of powdery mildew fungus diseases of foliage, fruit and stems of growing plants without damage to the host.

The compounds of this invention provide protection from damage caused by powdery mildew fungi when applied to the plants by the methods described hereinafter and at a sufficient rate to exert the desired fungicidal effect. They are especially suited for the protection of living plants.

Living plants are protected from fungi by applying one or more of the compounds of this invention to the soil in which they are growing or in which they may subsequently be seeded or planted; or to plant reproductive parts prior to planting; as well as to foliage, stems and fruit of the living plant. Living plants can also be protected by dipping the root system or physically injecting the chemical or chemicals into roots or stems.

Soil applications are made from dusts, granules, pellets, slurries or solution. Rates for application of the compounds of this invention to soil in which plants are or will be growing range from 1 to 100 parts per million by weight of the soil in which the roots are or will be growing.

Rates for application to seeds, tubers, bulbs or other plant reproductive parts, range fromm 10 to 1000 grams of active compound of this invention per 50 kilograms of planting material treated. Applications are made from dusts, slurries or solutions.

Rates for application of the compounds of this invention to foliage, stems and fruit of living plants range from 0.1 to 10 kilograms of active ingredient per hectare. The optimum amount within this range depends upon a number of variables which are well known to those skilled in the art of plant protection. These variables include, but are not limited to, the disease to be controlled, weather conditions expected, the type of crop, stage of development of the crop, and the interval between applications. Applications within the range given may need to be repeated one or many more times at intervals of 1 to 60 days. Applications are made from dusts, slurries or solutions.

The compositions of the invention can contain, in addition to the active ingredient of this invention, conventional insecticides, miticides, bactericides, nematicides, fungicides, or other agricultural chemicals such as fruit set agents, fruit thinning compounds, fertilizer ingredients and the like, so the compositions can serve useful purposes in addition to the control of fungi. The proper choice of amounts is readily made by one skilled in the art of protecting plants from pest depredations.

The outstanding control of powdery mildew by the compounds of this invention was illustrated by a greenhouse preventive test. The compounds listed in the following table were sprayed as water suspensions on cucumber seedlings to the point of run-off. Treated seedlings were dried and inoculated with conidia of the fungus, Erysiphe cichoracearum. After 8 days incubation in a greenhouse, seedlings which were not treated were 85 to 100 percent covered with powdery mildew. Disease control readings were made by estimating the percentage of leaf surface free of disease.

| Active Compound | Percent Powdery Mildew Control Concentration of Active Compound | | |
|---|---|---|---|
| | 80 PPM | 16 PPM | 3.2 PPM |
| 3-amino-6-chloro-2-propionamidoquinoxaline | 100 | 100 | 93 |
| 2-acetamido-3-amino-quinoxaline | 96 | 53 | 10 |
| 6-chloro-3-hexanamido-2-propionamidoquinoxaline | 100 | 100 | 86 |

The systemic activity of the compounds of this invention was demonstrated in a soil drench test on potted cucumber seedlings. Suspensions of 3-amino-6-chloro-2-propionamidoquinoxaline or 6-chloro-3-hexanamido-2-propionamidoquinoxaline were drenched on the soil at rates equivalent to 5 ppm and 1 ppm of active ingredient by weight of dry soil. Care was taken to avoid contact with the foliage by any of the treatments. The seedlings were inoculated with conidia of Erysiphe cichoracearum and incubated in the greenhouse until untreated plants were covered with disease. Disease control readings were made by estimating the percentage of leaf surface free of disease. The untreated plants were 95% covered with powdery mildew. Cucumber plants growing in soil containing 1 ppm of either of the test chemicals supported only an occasional mildew colony (90% control). Cucumber plants growing in soil containing 5 ppm of either of the test chemicals were free of mildew (100% control).

The preventive control of another powdery mildew on apple seedlings was illustrated in a greenhouse test. A water suspension of 3-amino-6-chloro-2-propionamidoquinoxaline at 400 ppm was sprayed to the point of runoff on potted apple seedlings. The treated seedlings were dried and inoculated with conidia of the fungus Podosphaera leucotricha. After 10 days incubation in the greenhouse, seedlings which were not treated were more than 90% covered with powdery mildew. The treated plants had only an occasional fungus colony (97% control).

Useful formulations of the compounds of this invention can be prepared in conventional ways. They include dusts, granules, pellets, solutions, suspensions, emulsions, wettable powders, emulsifiable concentrates and the like. Many of these can be applied directly. Sprayable formulations can be extended in suitable media and used at spray volumes of from a few pints to several hundred gallons per acre. High-strength compositions are primarily used as intermediates for further formulation. The formulations, broadly, contain about 1% to 99% by weight of active ingredient(s) and at least one of a) about 0.1% to 20% surfactant(s) and b) about 5% to 99% solid or liquid diluent(s). More specifically, they will contain these ingredients in the following approximate proportions.

| | Percent by Weight | | |
|---|---|---|---|
| | Active Ingredient | Diluent(s) | Surfactant(s) |
| Wettable Powders | 20–90 | 0–74 | 1–10 |
| Oil Suspensions, Emulsions, Solutions (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| Granules and Pellets | 1–95 | 5–99 | 0–15 |
| High-Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable and are achieved by incorporation into the formulation or by tank mixing.

Typical solid diluents are described in Watkins, et al., Handbook of Insecticide Dust Diluents and Carriers, 2nd. Edn., Dorland Books, Caldwell, N. J. The more absorptive diluents are preferred for wettable powders and the denser ones for dusts. Typical liquid diluents and solvents are described in Marsden, Solvents Guide, 2nd. Edn., Interscience, New York, 1950. Solubility under 0.1% is preferred for suspension concentrates; solution concentrates are preferably stable against phase separation at 0° C. McCutcheon's Detergents and Emulsifiers Annual, Allured Publ. Corp., Ridgewood, New Jersey, as well as Sisely and Wood, Encyclopedia of Surface Active Agents, Chemical Publ. Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147*ff*. and *Perry's Chemical Engineer's Handbook*, 4th. Edn., McGraw-Hill, N.Y., 1963, pp. 8–59*ff*.

For further information regarding the art of formulation see for example:

J. B. Buchanan, U.S. Pat. No. 3,576,834, Apr. 27, 1971, Col. 5 Line 36 through Col. 7 Line 70 and Ex. 1–4, 17, 106, 123–140.

R. R. Shaffer, U.S. Pat. No. 3,560,616, Feb. 2, 1971, Col. 3 Line 48 through Col. 7 Line 26 and Examples 3–9, 11–18.

E. Somers, "Formulation", Chapter 6 in Torgeson, "Fungicides", Vol. I, Academic Press, New York, 1967.

The following examples further illustrate the formulation of compositions within the scope of this invention.

EXAMPLE 6

| Wettable Powder | |
|---|---|
| 3-amino-6-chloro-2-propionamidoquinoxaline | 40 % |
| dioctyl sodium sulfosuccinate | 1.5 % |
| sodium ligninsulfonate | 3 % |
| low-viscosity methyl cellulose | 1.5 % |
| attapulgite | 54 % |

The ingredients are thoroughly blended, passed through an air mill, to produce an average particle size under 15 microns reblended, and sifted through a U.S.S. No. 50 sieve (0.3 mm opening) before packaging.

All compounds of the invention may be formulated in the same manner.

EXAMPLE 7

| Aqueous Suspension | |
|---|---|
| 3-amino-6-chloro-2-propionamidoquinoxaline | 25 % |
| hydrated attapulgite | 3 % |
| crude calcium ligninsulfonate | 10 % |
| sodium dihydrogen phosphate | 0.5 % |
| water | 61.5 % |

The ingredients are ground together in a ball or roller mill until the solid particles have been reduced to diameters under 10 microns.

EXAMPLE 8

| Oil Suspension | |
|---|---|
| 2-acetamido-3-aminoquinoxaline | 25 % |
| polyoxyethylene sorbitol hexaoleate | 5 % |
| highly aliphatic hydrocarbon oil | 70 % |

The ingredients are ground together in a sand mill until the solid particles have been reduced to under about 5 microns. The resulting thick suspension may be applied directly, but preferably after being extended with oils or emulsified in water.

EXAMPLE 9

| Granule | |
|---|---|
| wettable powder of Example 6 | 15 % |
| gypsum | 69 % |
| potassium sulfate | 16 % |

The ingredients are blended in a rotating mixer and water sprayed on to accomplish granulation. When most of the material has reached the desired range of 1.0 to 0.42 mm. (U.S.S. No. 18 to 40 sieves), the granules are removed, dried, and screened. Oversize material is crushed to produce additional material in the desired range. These granules contain 12% active ingredient.

EXAMPLE 10

| Dust | |
|---|---|
| 6-chloro-3-hexanamido-2-propionamido-quinoxaline | 10 % |
| attapulgite | 10 % |
| talc | 80 % |

The active ingredient is blended with attapulgite and then passed through a hammermill to produce particles substantially all below 200 microns. The ground concentrate is then blended with powdered talc until homogeneous.

EXAMPLE 11

| Wettable Powder | |
|---|---|
| 6-chloro-3-hexanamido-2-propionamido-quinoxaline | 50 % |
| sodium alkylnaphthalene sulfonate | 5 % |
| partially desulfonated sodium lignosulfonate | 3 % |
| kaolinite clay | 42 % |

The ingredients are blended, coarsely hammermilled and then air-milled to produce particles of active which are less than 20 microns in diameter. The product is reblended before packaging.

I claim:

1. A fungicidal composition comprising:
   a. a fungicidally effective amount of a compound of the formula:

[Chemical structure: quinoxaline derivative with substituents $R_2$, $NHCR_1$ (C=O), and $N(H)_{2-n}(C(=O)R_3)_n$]

wherein
R₁ is alkyl of 1 to 4 carbon atoms, cycloalkyl of 3 to 6 carbon atoms, alkenyl of 2 to 4 carbon atoms, ethynyl, alkoxyalkyl of 2 to 3 carbon atoms, chloroalkyl of 1 to 2 carbon atoms, bromoalkyl of 1 to 2 carbon atoms or cyanoalkyl of 2 to 3 carbon atoms;

R₂ is hydrogen, chlorine, bromine or fluorine;

R₃ is alkyl of 1 to 7 carbon atoms or alkenyl of 2 to 4 carbon atoms; and $n$ is 0 or 1; provided that the total number of carbon atoms in R₁ and R₃ is less than or equal to nine; and b. at least one of the following: a surfactant, or a solid or liquid diluent.

2. The composition of claim 1 wherein R₁ is alkyl of 2 to 3 carbon atoms, R₂ is chlorine, and $n = 0$.

3. The composition of claim 1 in which the compound is 3-amino-6-chloro-2-propionamidoquinoxaline.

4. The composition of claim 1 wherein $n$ is 1, R₁ is alkyl of 1 to 2 carbon atoms, R₂ is chlorine and R₃ is alkyl of 1 to 5 carbon atoms.

5. The composition of claim 1 in which the compound is 6-chloro-3-hexanamido-2-propionamidoquinoxaline.

6. A method of controlling injury to plants due to fungi which comprises applying to the plants to be protected a fungicidally effective amount of a compound of the formula:

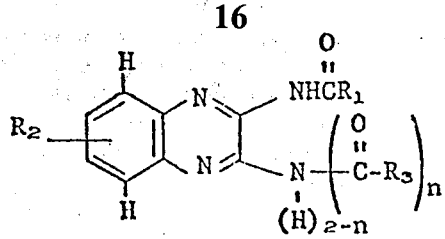

wherein
R₁ is alkyl of 1 to 4 carbon atoms, cycloalkyl of 3 to 6 carbon atoms, alkenyl of 2 to 4 carbon atoms, ethynyl, alkoxyalkyl of 2 to 3 carbon atoms, chloroalkyl of 1 to 2 carbon atoms, bromoalkyl of 1 to 2 carbon atoms or cyanoalkyl of 2 to 3 carbon atoms;

R₂ is hydrogen, chlorine, bromine or fluorine;

R₃ is alkyl of 1 to 7 carbon atoms or alkenyl of 2 to 4 carbon atoms; and $n$ is 0 or 1; provided that the total number of carbon atoms in R₁ and R₃ is less than or equal to nine.

7. The method of claim 6 wherein R₁ is alkyl of 2 to 3 carbon atoms, R₂ is chlorine and $n$ is 0.

8. The method of claim 6 in which the compound is 3-amino-6-chloro-2-propionamidoquinoxaline.

9. The method of claim 6 wherein $n$ is 1, R₁ is alkyl of 1 to 2 carbon atoms, R₂ is chlorine, and R₃ is alkyl of 1 to 5 carbon atoms.

10. The method of claim 6 in which the compound is 6-chloro-3-hexanamido-2-propionamidoquinoxaline.

* * * * *